United States Patent
Watanabe et al.

(10) Patent No.: US 8,475,740 B2
(45) Date of Patent: Jul. 2, 2013

(54) LIQUID DISPENSING APPARATUS

(75) Inventors: Atsushi Watanabe, Hitachinaka (JP);
Shigeki Matsubara, Hitachinaka (JP);
Takuya Yamaguchi, Hitachinaka (JP);
Masaaki Odakura, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 472 days.

(21) Appl. No.: 12/120,426

(22) Filed: May 14, 2008

(65) Prior Publication Data

US 2008/0286158 A1    Nov. 20, 2008

(30) Foreign Application Priority Data

May 15, 2007   (JP) .................................. 2007-129293

(51) Int. Cl.
| | | |
|---|---|---|
| *B01L 3/00* | (2006.01) | |
| *G01F 19/00* | (2006.01) | |
| *G01N 27/22* | (2006.01) | |
| *G01N 1/10* | (2006.01) | |
| *G01N 1/14* | (2006.01) | |
| *G01N 35/10* | (2006.01) | |

(52) U.S. Cl.
USPC ............ 422/521; 422/400; 422/519; 73/1.73; 73/1.74; 73/335.04; 73/864.11; 73/864.24; 436/180

(58) Field of Classification Search
USPC .................. 422/400, 519, 521; 73/1.73, 1.74, 73/335.04, 864.11, 864.24
See application file for complete search history.

(56) References Cited

U.S. PATENT DOCUMENTS

| | | | | |
|---|---|---|---|---|
| 4,844,887 | A | * | 7/1989 | Galle et al. ...................... 422/65 |
| 5,855,851 | A | * | 1/1999 | Matsubara et al. ........... 422/511 |
| 6,713,021 | B1 | * | 3/2004 | Shvets et al. ................... 422/502 |
| 7,182,912 | B2 | * | 2/2007 | Carey et al. ...................... 422/64 |
| 7,387,356 | B2 | * | 6/2008 | Shinkawa et al. ................ 347/19 |
| 7,670,564 | B2 | * | 3/2010 | Yoshida et al. ............... 422/106 |
| 2003/0203494 | A1 | | 10/2003 | Hyde et al. |
| 2004/0034479 | A1 | * | 2/2004 | Shimase et al. .................. 702/19 |
| 2005/0223814 | A1 | * | 10/2005 | Shvets et al. ............... 73/861.08 |
| 2006/0105359 | A1 | * | 5/2006 | Favuzzi et al. ..................... 435/6 |
| 2006/0166373 | A1 | * | 7/2006 | Enoki et al. .................... 436/180 |
| 2007/0144253 | A1 | * | 6/2007 | Kobayashi .................. 73/304 C |

FOREIGN PATENT DOCUMENTS

| | | |
|---|---|---|
| EP | 0526210 | 2/1993 |
| EP | 526210 A1 * | 2/1993 |
| EP | 0984284 | 3/2000 |

(Continued)

OTHER PUBLICATIONS

CN Office Action in Application No. 200810107830.9, dated Jun. 26, 2012.

*Primary Examiner* — Bobby Ramdhanie
*Assistant Examiner* — Jennifer Wecker
(74) *Attorney, Agent, or Firm* — Mattingly & Malur, PC

(57) ABSTRACT

A liquid dispensing apparatus is provided which makes it possible to correctly and easily detect a dispensing operation judgment failure with high accuracy without particularly using a complicated detection mechanism or means. The liquid dispensing apparatus includes a nozzle which sucks a solution in a cassette and dispenses the sucked solution into another cassette; and a cassette holder which holds the another cassette, and the nozzle is used as a first electrode and the cassette holder as a second electrode. Further, the liquid dispensing apparatus has measurement means for measuring a capacitance between the first and second electrodes during a solution dispensing operation.

5 Claims, 20 Drawing Sheets

$C = \varepsilon S/d$
$\varepsilon$ = DIELECTRIC CONSTANT
$S$ = AREA
$d$ = DISTANCE

FOREIGN PATENT DOCUMENTS

| | | |
|---|---|---|
| EP | 1710587 | 10/2006 |
| JP | 62-218818 | 9/1987 |
| JP | 63-259420 | 10/1988 |
| JP | 2-059619 | 2/1990 |
| JP | 3-40343 | 6/1991 |
| JP | 8-114604 | 5/1996 |
| JP | 11-271320 A | 10/1999 |
| JP | 2003-344432 A | 12/2003 |
| WO | 91/16675 | 10/1991 |

* cited by examiner $C = \varepsilon S/d$ $\varepsilon$ = DIELECTRIC CONSTANT
S = AREA
d = DISTANCE

FIG.4

[WAVEFORM FAILURE JUDGMENT]   FAILED : ×  , NORMAL : ○

| NUMBER OF TESTS | ABSORBANCE | DIGITAL WAVEFORM FAILURE | ANALOG WAVEFORM FAILURE | FAILURE JUDGMENT | NUMBER OF TESTS | ABSORBANCE | DIGITAL WAVEFORM FAILURE | ANALOG WAVEFORM FAILURE | FAILURE JUDGMENT |
|---|---|---|---|---|---|---|---|---|---|
| 1 | 8670 | ○ | ○ | NORMAL | 51 | 8767 | ○ | ○ | NORMAL |
| 2 | 9337 | × | × | FAILURE | 52 | 8696 | ○ | ○ | NORMAL |
| 3 | 9674 | × | × | FAILURE | 53 | 8770 | ○ | ○ | NORMAL |
| 4 | 9369 | × | × | FAILURE | 54 | 8762 | ○ | ○ | NORMAL |
| 5 | 9539 | × | × | FAILURE | 55 | 8716 | ○ | ○ | NORMAL |
| 6 | 9500 | × | × | FAILURE | 56 | 8749 | ○ | ○ | NORMAL |
| 7 | 9670 | × | × | FAILURE | 57 | 8805 | ○ | ○ | NORMAL |
| 8 | 9640 | × | × | FAILURE | 58 | 8792 | ○ | ○ | NORMAL |
| 9 | 9580 | × | × | FAILURE | 59 | 8752 | ○ | ○ | NORMAL |
| 10 | 9446 | × | × | FAILURE | 60 | 8826 | ○ | ○ | NORMAL |
| 11 | 9741 | × | × | FAILURE | 61 | 8764 | ○ | ○ | NORMAL |
| 12 | 9509 | × | × | FAILURE | 62 | 8741 | ○ | ○ | NORMAL |
| 13 | 9627 | × | × | FAILURE | 63 | 8731 | ○ | ○ | NORMAL |
| 14 | 9471 | × | × | FAILURE | 64 | 8768 | ○ | ○ | NORMAL |
| 15 | 9870 | × | × | FAILURE | 65 | 8709 | ○ | ○ | NORMAL |
| 16 | 9602 | × | × | FAILURE | 66 | 8728 | ○ | ○ | NORMAL |
| 17 | 9589 | × | × | FAILURE | 67 | 8778 | ○ | ○ | NORMAL |
| 18 | 9575 | × | × | FAILURE | 68 | 8740 | ○ | ○ | NORMAL |
| 19 | 9520 | × | × | FAILURE | 69 | 8793 | ○ | ○ | NORMAL |
| 20 | 9659 | × | × | FAILURE | 70 | 8764 | ○ | ○ | NORMAL |
| 21 | 9757 | × | × | FAILURE | 71 | 8761 | ○ | ○ | NORMAL |
| 22 | 9590 | × | × | FAILURE | 72 | 8815 | ○ | ○ | NORMAL |
| 23 | 9632 | × | × | FAILURE | 73 | 8763 | ○ | ○ | NORMAL |
| 24 | 9857 | × | × | FAILURE | 74 | 8734 | ○ | ○ | NORMAL |
| 25 | 9538 | × | × | FAILURE | 75 | 8736 | ○ | ○ | NORMAL |
| 26 | 9661 | × | × | FAILURE | 76 | 8776 | ○ | ○ | NORMAL |
| 27 | 9575 | × | × | FAILURE | 77 | 8746 | ○ | ○ | NORMAL |
| 28 | 9726 | × | × | FAILURE | 78 | 8730 | ○ | ○ | NORMAL |
| 29 | 9436 | × | × | FAILURE | 79 | 8747 | ○ | ○ | NORMAL |
| 30 | 9688 | × | × | FAILURE | 80 | 8748 | ○ | ○ | NORMAL |
| 31 | 9297 | × | × | FAILURE | 81 | 8746 | ○ | ○ | NORMAL |
| 32 | 9525 | × | × | FAILURE | 82 | 8763 | ○ | ○ | NORMAL |
| 33 | 9330 | × | × | FAILURE | 83 | 8772 | ○ | ○ | NORMAL |
| 34 | 9423 | × | × | FAILURE | 84 | 8779 | ○ | ○ | NORMAL |
| 35 | 9153 | × | × | FAILURE | 85 | 8742 | ○ | ○ | NORMAL |
| 36 | 9244 | × | × | FAILURE | 86 | 8766 | ○ | ○ | NORMAL |
| 37 | 9197 | × | × | FAILURE | 87 | 8750 | ○ | ○ | NORMAL |
| 38 | 9131 | × | × | FAILURE | 88 | 8838 | ○ | ○ | NORMAL |
| 39 | 9095 | × | × | FAILURE | 89 | 8761 | ○ | ○ | NORMAL |
| 40 | 8987 | × | × | FAILURE | 90 | 8771 | ○ | ○ | NORMAL |
| 41 | 8896 | ○ | × | FAILURE | 91 | 8776 | ○ | ○ | NORMAL |
| 42 | 8856 | ○ | × | FAILURE | 92 | 8753 | ○ | ○ | NORMAL |
| 43 | 8895 | × | × | FAILURE | 93 | 8776 | ○ | ○ | NORMAL |
| 44 | 8797 | ○ | ○ | NORMAL | 94 | 8776 | ○ | ○ | NORMAL |
| 45 | 8925 | × | × | FAILURE | 95 | 8785 | ○ | ○ | NORMAL |
| 46 | 8747 | ○ | ○ | NORMAL | 96 | 8773 | ○ | ○ | NORMAL |
| 47 | 8822 | ○ | ○ | NORMAL | 97 | 8792 | ○ | ○ | NORMAL |
| 48 | 8739 | ○ | ○ | NORMAL | 98 | 8792 | ○ | ○ | NORMAL |
| 49 | 8888 | ○ | × | FAILURE | 99 | 8790 | ○ | ○ | NORMAL |
| 50 | 8759 | ○ | × | NORMAL | 100 | 8771 | ○ | ○ | NORMAL |

LIQUID DISPENSING APPARATUS

BACKGROUND OF THE INVENTION

1. Field of the Invention

The present invention relates to a liquid dispensing apparatus, and more particularly to a liquid dispensing apparatus having a liquid surface detection function suitable for sampling of a reagent, a sample, or a reaction solution of the reagent and the sample in an automated analyzer.

2. Description of the Related Art

An automated analyzer, such as a biochemistry analyzer, an immunological analyzer, etc., is provided with a dispensing apparatus which automatically performs suction and discharge (hereinafter abbreviated to dispensing) of a liquid sample and reagent from sample and reagent cassettes, respectively, to a vessel.

In particular, a biochemistry analyzer performs the steps of: dispensing a biological sample, such as blood, urine, etc., to a first or second cassette storing a sample; further dispensing a reagent from a third cassette storing a reagent to the second cassette into which the biological sample was dispensed; and measuring a color change produced in a mixture of the sample and the reagent by use of measurement means such as a photometer.

During sample and reagent dispensing operations, the leading end of a dispensing probe is immersed into a solution to be dispensed. The larger the depth (immersion depth) with which the leading end of the dispensing probe is immersed, then the larger the amount of solution which adheres to an outer wall of the dispensing probe, and the larger the contamination between different samples and reagents.

Then, in order to reduce the immersion depth of the dispensing probe as much as possible, such an operation control technique is commonly performed that includes the steps of: detecting a liquid surface in a cassette; stopping the lowering operation of the probe at a timing when the leading end of the probe has reached a position slightly below the liquid surface; and sucking a predetermined quantity of solution into the probe.

A technique for correctly detecting a liquid surface is important for such operation. Examples of a proposed technique for detecting a liquid surface includes a method of measuring a capacitance between the dispensing probe and the solution, a method of measuring pressure changes in the dispensing probe, and the like.

Analyzers using any of these methods are disclosed, for example, in JP-A-62-218818, JP-A-63-259420, JP-A-2-59619, and JP-A-8-114604.

Although the above-mentioned conventional methods use different liquid surface detection methods, each method detects whether or not a sample and a reagent solution exist at the start of suction and suction starts when the existence thereof is recognized or when the probe is moved to a position at which the existence thereof is assumed. Therefore, even if a necessary quantity of solution cannot be sucked or the sample or the reagent solution runs out during the suction operation, these states cannot be directly sensed.

As a method of detecting the above-mentioned suction state, a technique which detects whether or not a sample or a reagent solution is actually sucked by using a pressure sensor is known in JP-B-3-40343.

However, with such a method of using a pressure sensor, if the quantity of suction is very small, a sufficient pressure change cannot be obtained, thus making it difficult to correctly detect the above-mentioned state.

SUMMARY OF THE INVENTION

As described in above-mentioned JP-A-8-114604, a liquid dispensing apparatus which detects a liquid surface based on a capacitance, checks the existence of a solution, and performs a suction operation is known. However if the liquid surface has bubbled, for example, even this apparatus may erroneously detect a bubble as a liquid surface and suck not the solution but the bubble or air.

There has been no effective means for directly detecting a solution suction failure caused by such erroneous detection of a liquid surface and a solution dispensing failure resulting therefrom. Further, with a method of using a pressure sensor disclosed in above-mentioned JP-B-3-40343, if the quantity of suction is very small, a sufficient pressure change cannot be obtained, thus making it impossible to correctly detect a dispensing failure.

Further, from a viewpoint of improvement in operability of a liquid dispensing apparatus, it is needed to immediately inform an operator of an analysis failure caused by the above-mentioned dispensing failure.

Further, if it is possible to prompt the operator to perform a re-inspection in which an analysis failure occurred, the relevant re-inspection can be performed without delay.

In view of the above-mentioned drawbacks, an object of the present invention is to provide a liquid dispensing apparatus which makes it possible to correctly and easily perform judgment on a dispensing operation failure with high accuracy without particularly using a complicated detection mechanism or means.

The present invention provides a liquid dispensing apparatus comprising: a nozzle which sucks a solution in a cassette and dispenses the sucked solution into another cassette; and a cassette holder which holds another cassette; wherein the nozzle is used as a first electrode and the cassette holder as a second electrode; and wherein the liquid dispensing apparatus includes measurement means for measuring a capacitance between the first and second electrodes between the time before the start of solution dispensing operation and the time immediately after the end thereof.

In accordance with the present invention, it is possible to correctly and easily accomplish a dispensing operation failure judgment with high accuracy by measuring an electrical physical quantity during a dispensing operation. Further, when the result of the dispensing operation failure judgment is failure, an alarm is added to an analysis result to prevent an inspection result other than an expected value. Further, the operator is notified of a re-inspection request for an inspection in which an alarm occurred. This makes it possible to shorten the time it takes to report the inspection result.

BRIEF DESCRIPTION OF THE DRAWINGS

FIG. 4 is a table showing results of dispensing operation failure judgment summarized based on an analysis result in a case where a dispensing operation failure occurs and a result of capacitance supervision during solution dispensing operation according to an embodiment of the present invention.

DETAILED DESCRIPTION OF THE PREFERRED EMBODIMENTS

Embodiments of the present invention will be explained below with reference to the accompanying drawings sequentially from FIG. 1.

Figure 1:
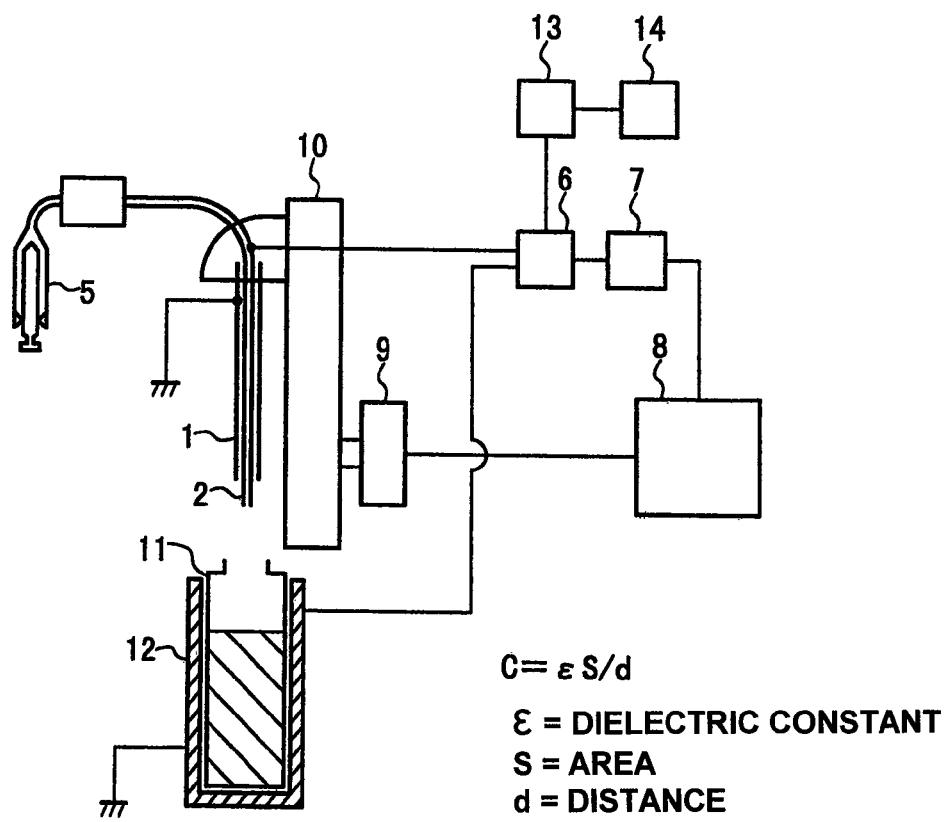
FIG. 1 is a schematic diagram showing the configuration of a liquid dispensing apparatus according to an embodiment of the present invention.

FIG. 1 shows an embodiment of a liquid dispensing apparatus according to the present invention.

A nozzle has a coaxial double pipe structure composed of a moving medium pipe (tube) 2 which is an inner portion of the nozzle, and an electric shield 1.

The shield 1 and the tube 2 which are structural parts of the nozzle are made of a conductive material such as a stainless steel, and the shield 1 is grounded.

The leading end of the nozzle (leading end of the tube 2) is a portion which sucks and dispenses a sample, a reagent, or a reaction solution thereof (hereafter simply referred to as solution).

Further, the nozzle is covered by the conductive shield 1 to minimize an exposure area of the leading end of the nozzle (leading end of the tube 2) which is one detection electrode, thus reducing an effect of a capacitance between a portion other than a second cassette holder 12 which is another electrode for the nozzle and the nozzle on measurement.

Further, the shield 1 is used also as a magnetic shield, thus preventing malfunction of liquid surface detection caused by outside noise such as that produced by a motor 9.

The nozzle can be vertically moved by controlling a nozzle vertical motion mechanism 10 in association with a control unit 8 and the motor 9. A first cassette 11 into which a solution is to be dispensed is stored in the first cassette holder 12.

The first cassette holder 12 is made of a conductive material such as aluminum, and grounded. The tube 2 and the first cassette holder 12 are connected to a capacitance measurement unit as two capacitive-type electrodes.

Liquid surface detection can be performed by measuring a capacitance between the electrodes.

The tube 2 on the nozzle side serves as a first electrode, and the first cassette holder 12 serves as a second electrode. A capacitance measurement unit 6, which is an electrical-physical-quantity measurement means, measures and detects a capacitance between the two electrodes.

Further, it is also possible to replace the second electrode with the first cassette 11 into which a solution is to be dispensed from the first cassette holder 12. In this case, a cassette is made of a conductive material, such as stainless steel, aluminum, etc.

A liquid surface judgment unit 7 is connected between the capacitance measurement unit 6 and the control unit 8. The liquid surface judgment unit 7 determines whether or not the leading end of the nozzle is in contact with the liquid surface in a cassette.

The operation of the liquid dispensing apparatus will be explained below.

The nozzle is lowered by the vertical motion mechanism 10 in order to suck a solution in the first cassette.

The capacitance measurement unit 6 measures a capacitance between the tube 2 and the first cassette holder which are detection electrodes, and transmits an output signal to the liquid surface judgment unit 7. The capacitance between the two electrodes is measured by the electrical-physical-quantity measurement means (capacitance measurement unit 6).

If the leading end of the nozzle is lowered by the nozzle vertical motion mechanism 10 and comes in contact with the liquid surface, the liquid surface judgment unit 7 transmits a liquid surface detection signal to the control unit 8. In response to the liquid surface detection signal, the control unit 8 stops the motor 9 so that the nozzle is no longer lowered.

The two electrodes are also provided with a function as liquid surface detection means for detecting a liquid surface.

With the leading end of the nozzle in contact with the liquid surface, a predetermined quantity of solution in the first cassette is sucked into the tube 2 through the operation of a syringe 5.

Subsequently, the nozzle is raised by the elevating operation of the nozzle vertical motion mechanism 10, horizontally moved by the nozzle horizontal motion mechanism (not shown), and then lowered onto a second cassette 11 by the nozzle vertical motion mechanism 10.

After the nozzle is lowered onto the second cassette 11, the solution sucked by the tube 2 is dispensed into the second cassette 11 by the operation of a syringe 5.

The tube 2 is filled with a moving medium (solution) such as water, and the solution which moves in response to the operation of the syringe 5 is a suction and dispensing medium.

When a solution is to be sucked in the tube 2 of the nozzle, the control unit 8 controls the nozzle vertical operation and syringe operation so that the surface of the sucked solution does not come in contact with the tube 2 and the moving medium therein.

When the solution sucked into the tube 2 of the nozzle is dispensed into the second cassette 11, the capacitance between the tube 2 and the second cassette holder 12 is measured, and the dispensing operation failure judgment is performed by a suction detector 13 based on a capacitance change.

If a dispensing operation failure occurs, the suction detector 13 transmits a relevant signal to an alarm generator 14, which generates an alarm.

Based on this alarm information, it is possible to take measures for an inspection in which a dispensing operation failure occurred, for example, a reinspection request.

The suction detector 13 is included in the failure judgment means for judging the mixing of a bubble or air during the dispensing operation. A judgment method performed by the failure judgment means including the suction detector 13 will be explained later.

Figure 2:
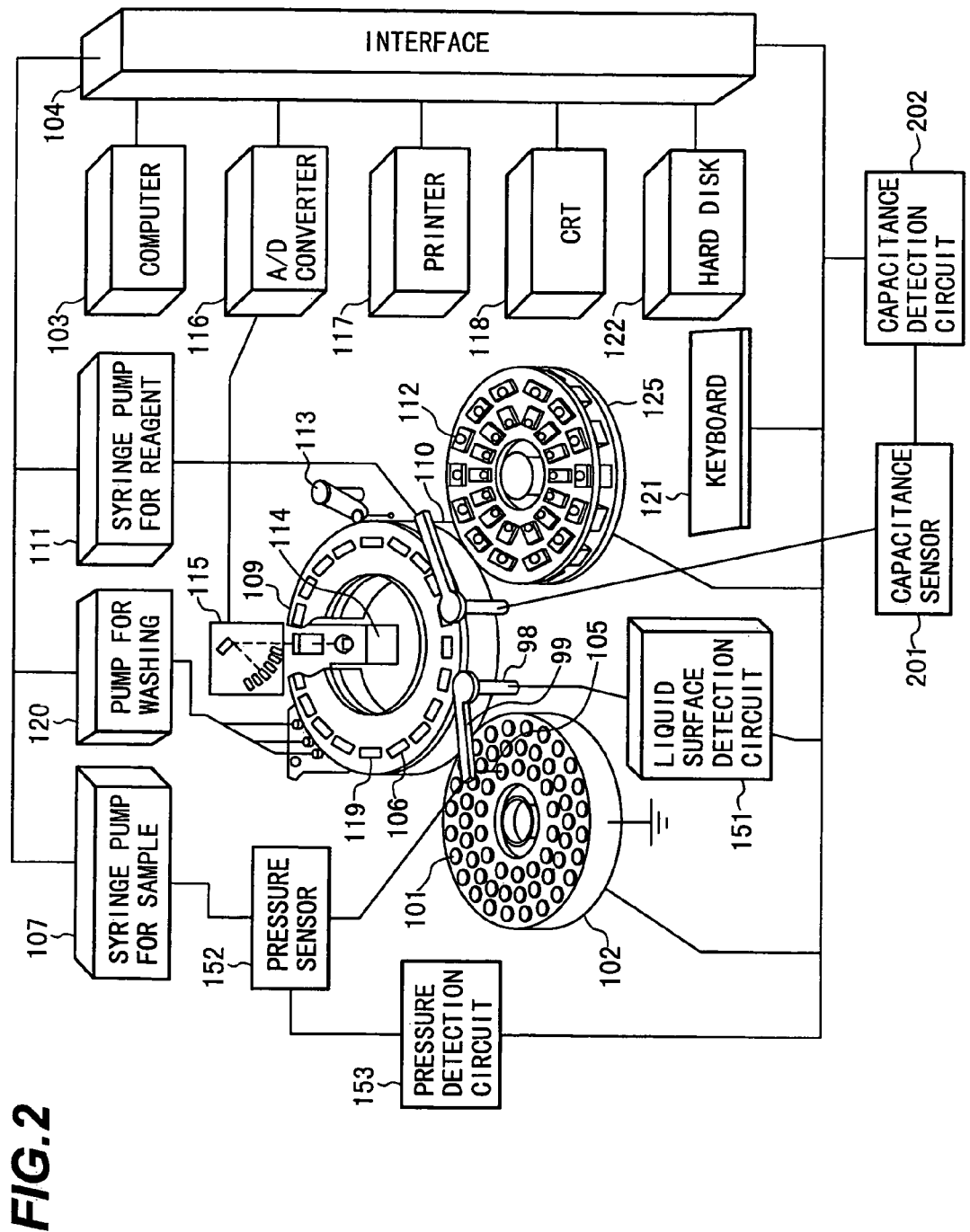
FIG. 2 is a schematic diagram showing the overall configuration of an automated analyzer to which the present invention is applicable.

FIG. 2 is a schematic diagram of an automated analyzer according to the present invention, showing a pipettor and peripheral portions thereof.

Since the configuration and the function of each part have a commonality with a conventional apparatus, description of details will be omitted.

A sample dispensing arm 99 of a sample pipettor 98 vertically moves and rotates.

A probe 105 attached to the sample dispensing arm 99 sucks a sample in a sample cassette 101 arranged on a sample compartment 102 which rotates clockwise and counterclockwise, and dispenses the sample into a vessel 106.

At the leading end of the probe 105, a nozzle for sucking and dispensing a sample is provided so as to be vertically suspended.

As can be seen from FIG. 2, the structure for arranging sample cassettes 101 on the sample compartment 102 is commonly applicable to a universal arrangement which makes it possible to arrange a sample cassette 101 directly on the sample compartment 102, and place a sample cassette 101 on a test tube (not shown).

The configuration of the automated analyzer of FIG. 2 will be further explained below.

Reagent bottles 112 associated with a plurality of analysis items to be subjected to analysis are arranged on a rotatable reagent compartment 125. A predetermined quantity of reagent is dispensed from a reagent bottle 112 to a vessel 106 by the probe attached to a movable arm of a reagent pipettor 110.

At the leading end of the probe of the reagent pipettor, a nozzle for sucking and dispensing a reagent is provided so as to be vertically suspended.

The probe 105 of the sample pipettor performs sample suction and dispensing operations in conjunction with the operation of the syringe pump 107 for the sample. The probe of the reagent pipettor 110 performs reagent suction and dispensing operations in conjunction with the operation of the syringe pump 111 for the reagent.

Analysis items for each sample are inputted from an input apparatus, such as a keyboard 121, a screen of a CRT 118, etc. The operation of each unit in the automated analyzer is controlled by a computer 103.

With intermittent rotation of the sample compartment 102, a sample cassette 101 is transferred to a sample suction position and then stopped at the sample suction position. Then, the probe 105 of the sample pipettor is lowered into the sample cassette.

When the leading end of the probe 105 comes in contact with the surface of the sample solution through the lowering operation, a detection signal is outputted from a liquid surface detection circuit 151. Then, the computer 103 performs control so as to stop the lowering operation provided by a drive unit of the sample dispensing arm 99 based on the detection signal.

After a predetermined quantity of sample is sucked into the dispensing probe 105, the probe 105 of the pipettor is raised to a top dead center.

While the probe 105 of the pipettor is sucking a predetermined quantity of sample, a pressure sensor 152 detects fluctuations of the passage internal pressure during the suction operation produced in the passage between the probe 105 and the pump 107 for sample.

A pressure signal detected is supervised by a pressure detection circuit 153. If any abnormal state is detected in pressure fluctuations during suction operation, it is highly likely that the predetermined quantity of the sample has not been sucked. Therefore, an alarm is added to the analysis result to be issued after completing the analysis in order to draw the operator's attention.

After the predetermined quantity of sample has been sucked, the sample dispensing arm 99 horizontally swivels, lowers the probe 105 at a position of a vessel 106 on a reaction compartment 109, and dispenses the sucked sample into the vessel 106.

When the vessel 106 containing the sample is moved to a reagent accretion position, the probe of the reagent pipettor 110 dispenses a predetermined quantity of reagent from a reagent bottle 112 associated with a relevant analysis item to the vessel 106.

The above-mentioned reagent dispensing will be explained in detail below.

After the probe of the reagent pipettor 110 has sucked a predetermined quantity of reagent from the reagent bottle 112, it then dispenses the reagent into the vessel 106. In response to this dispensing operation, a capacitance sensor 201 implemented in the probe of the reagent pipettor 110 measures a capacitance between the probe and a cassette or a cassette holder.

The capacitance sensor 201 is formed by using the first and second electrodes, etc. mentioned earlier with reference to FIG. 1.

A signal measured by the capacitance sensor 201 is supervised by a capacitance detection circuit 202. If a capacitance failure is detected during the reagent dispensing operation, it is highly likely that the predetermined quantity of reagent has not been sucked, and therefore an alarm is added to the relevant analysis result.

The capacitance detection circuit 202 is formed by the capacitance measurement unit 6 and the suction detector 13 mentioned earlier with reference to FIG. 1. The capacitance detection circuit 202 is included in the failure judgment means for judging whether mixing of a bubble or air occurs during the dispensing operation.

The capacitance detection circuit 202 is controlled by the computer 103 as is each of other units.

During supervision of the dispensing operation mentioned in the above-mentioned embodiment, the probe of the sample pipettor measures fluctuations of the passage internal pressure during the sample suction operation, while the probe of the reagent pipettor measures a capacitance between the probe and a reagent cassette during the reagent dispensing operation. Alternatively, it is possible that the probe of the sample pipettor measures a capacitance between the probe and a sample cassette during the sample dispensing operation, while the probe of the reagent pipettor measures fluctuations of the passage internal pressure during the reagent suction operation.

Further, it is possible to perform measurement either at a suction or dispensing timing of the probe of the pipettor as a timing of supervision. With information used for failure judgment, it is possible to use either suction or dispensing or both by the probe of the pipettor.

The electrical conductivity and inductance may be used as an electrical physical quantity to be subjected to measurement in the dispensing operation. In this case, a signal sensor and a signal detection circuit are provided instead of the capacitance sensor and the capacitance detection circuit of FIG. 2. For example, when the result of flow rate measurement is used, a flow rate sensor and a flow rate detection circuit are provided.

Further, if magnetic particles are contained in a solution to be supervised, dispensing operation failure judgment may be performed by measuring a magnetic field intensity of the solution. In this case, a magnetic sensor and a magnetic detection circuit are provided instead of the capacitance sensor and the capacitance detection circuit of FIG. 2.

With dispensing operations of a sample and a reagent, the liquid surfaces of a sample in the sample cassette 101 and a reagent in the reagent bottle 112 are detected. A mixture in the vessel 106 to which the sample and the reagent are added is measured by a stirrer 113.

During the transfer of the vessel 106, a plurality of vessels 106 pass over a flux of light from a light source 114, and an absorbance or a luminescence value of each mixture is measured by a photometer 115 provided as the measurement means.

An absorbance signal passes through an A/D converter 116 and then an interface 104, and enters the computer 103 in which the concentration (analysis item) is calculated.

An analysis result is printed on a printer 117 or displayed on the screen of the CRT 118 in the display unit, through the interface 104, and at the same time stored in a hard disk 122 as a memory.

A sound-based alarm for failure can also be used in addition to a failure alarm which will be displayed on the display unit.

The vessel 106 subjected to photometry is washed at a position of a washing mechanism 119. A pump 120 for washing supplies cleaning water to the vessel 106 and discharges a reaction solution therefrom.

In the example of FIG. 2, three rows of cassette support portions are formed on the sample compartment 102 so as to concentrically arrange three rows of sample cassettes 101. A position at which the sample dispensing probe 105 sucks a sample is allocated for each row.

As means for judging a solution dispensing operation failure, the following explains a method of measuring a capacitance between the dispensing probe and a cassette or a cassette holder between the time before the start of solution dispensing operation and the time immediately after the end thereof, and performing dispensing operation failure judgment from a measurement result.

Figure 3A:
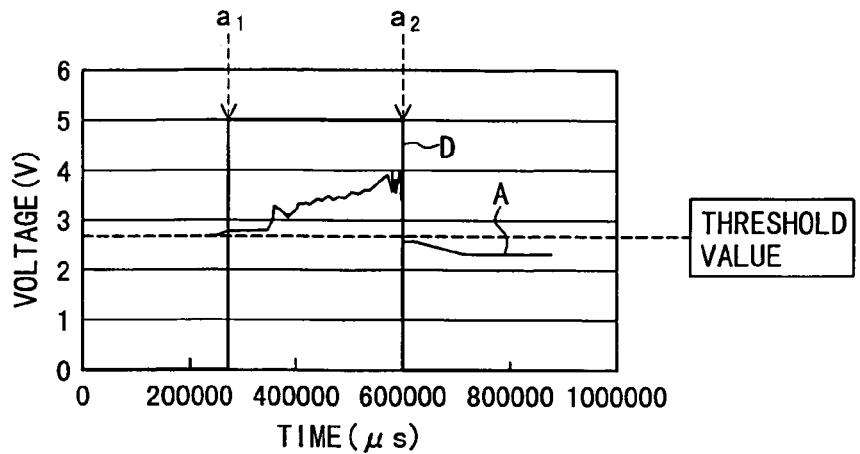
FIGS. 3A, 3B, and 3C show timing charts of a state during solution dispensing operation is supervised according to an embodiment of the present invention.
Figure 3B:
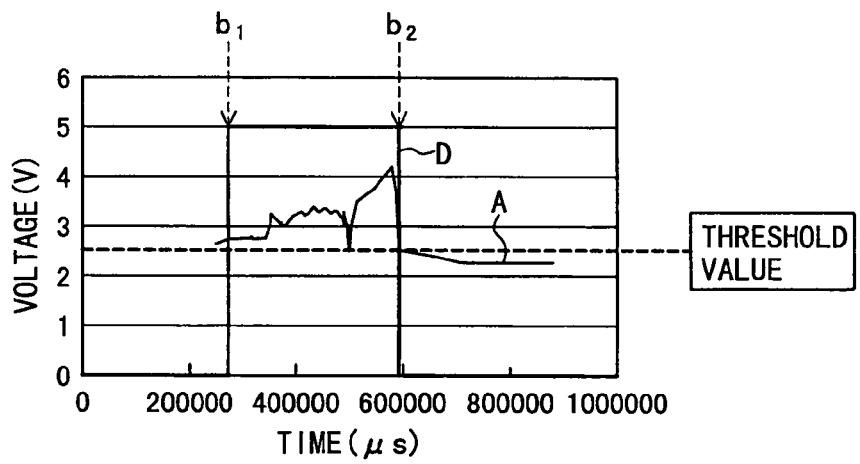
Figure 3C:
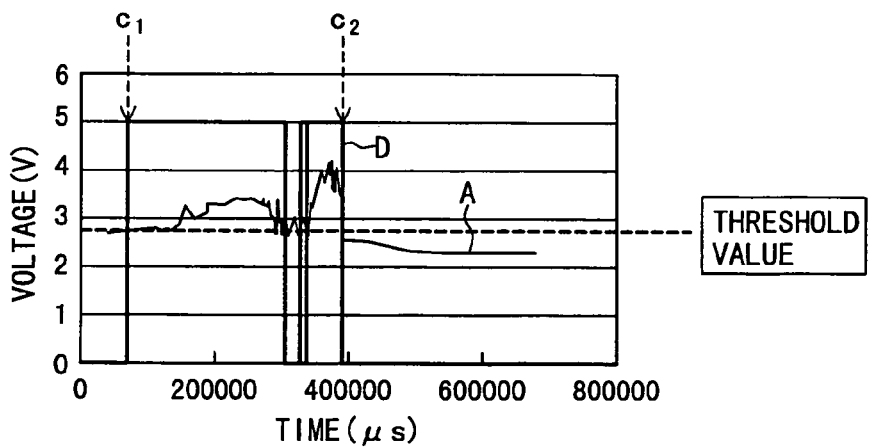
Figure 5:
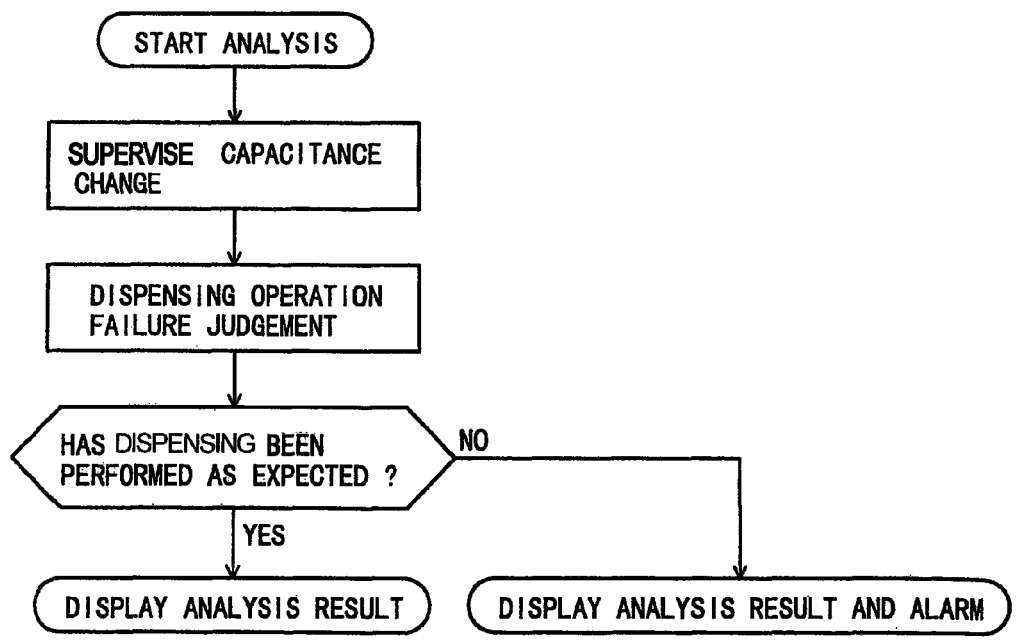
FIG. 5 is a diagram showing a flow chart from the start of analysis up to result display according to a first embodiment of the present invention.
Figure 6:
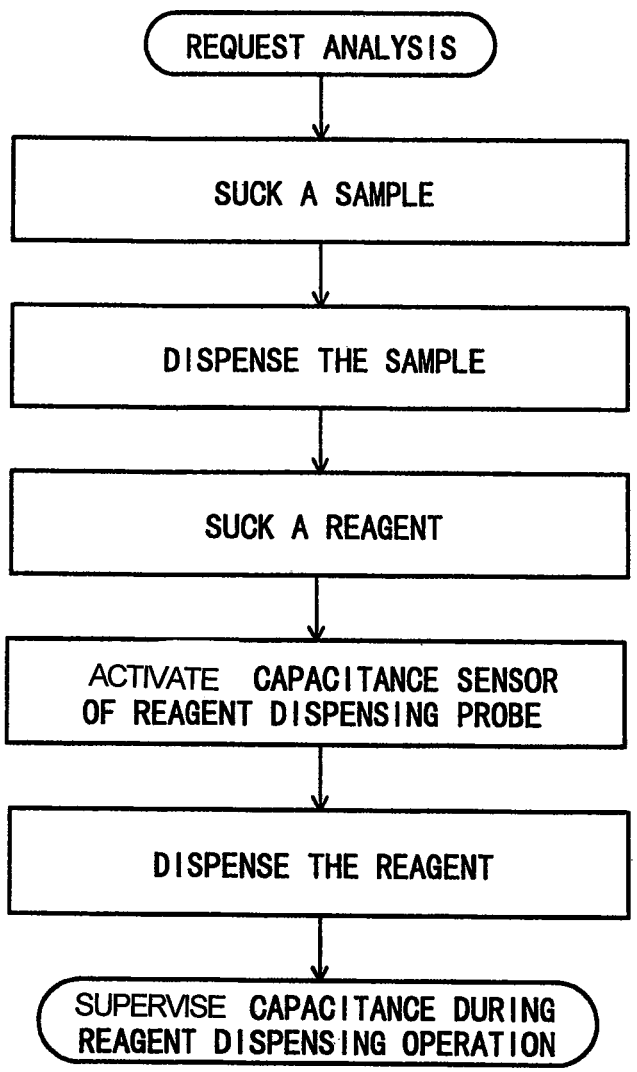
FIG. 6 is a diagram showing a flow chart up to capacitance measurement during reagent dispensing operation according to the first embodiment of the present invention.

FIGS. 3A, 3B, and 3C show results of the measurement of a capacitance between the dispensing probe and a cassette or between the dispensing probe and a cassette holder between the time before the start of the solution dispensing operation and the time immediately after the end thereof. FIG. 3A shows a capacitance when the quantity of dispensed solution coincides with a setup value; and FIGS. 3B and 3C, a capacitance when the quantity of the dispensed solution is below the setup value. Here, the setup value denotes a dispensing quantity registered in the application screen.

In each of graphs of FIGS. 3A, 3B, and 3C, the vertical axis is assigned a voltage converted from the capacitance and the horizontal axis time.

Reference symbols in the graphs will be explained below. Reference symbol A denotes an analog signal of the capacitance; and D, a digital signal of A. Each of the digital signal sections ($a_1$-$a_2$, $b_1$-$b_2$, and $c_1$-$c_2$) indicates a capacitance between the nozzle and a cassette or a cassette holder when the dispensing probe dispenses a solution into a vessel.

First, a capacitance when the probe dispenses a quantity of solution as specified by a setup value will be explained below.

Referring FIG. 3A, in a section from the start to the end of solution dispensing (section $a_1$-$a_2$), there is no failure in the analog and digital signals.

Referring to FIGS. 3B and 3C, for a capacitance when the probe dispenses a quantity of solution below the setup value, a failure can be seen in either the analog or digital signal or both.

In FIG. 3B, in a section from the start to the end of solution dispensing (section $b_1$-$b_2$), there is no failure in the digital signal but there is a capacitance change for which the threshold value exceeds the value of the analog signal.

In FIG. 3C, in a section from the start to the end of solution dispensing (section $c_1$-$c_2$), there is a capacitance change below the threshold value in the analog and digital signals.

Judgment means for failure judgment based on the result of the capacitance measurement will be explained in detail below. First of all, when a digital signal is used, dispensing operation failure judgment is performed first from the signal in the target section. For example, as shown in FIGS. 3A and 3B, there is no signal change in the digital signal in a section from the start to the end of the solution dispensing (sections $a_1$-$a_2$ and $b_1$-$b_2$, respectively). In this case, there is no voltage change in the section and therefore the dispensing operation is judged as normal. In contrast, as shown in FIG. 3C, the voltage becomes 0V in a section from the start to the end of solution dispensing (section $c_1$-$c_2$). In this case, there is a signal change in the section and therefore the dispensing operation is judged as failure. As mentioned above, in failure judgment using a digital signal, the dispensing operation failure judgment is performed based on whether or not there is a signal change in a section. Digital signal failure judgment is performed according to a flow chart shown in FIG. 8.

Failure judgment using an analog signal will be explained below. As means for judging a dispensing operation failure using an analog signal, signal waveform components are used. Components used include a section length (measurement time), a maximum output value, an output value at an arbitrary time, and a total number of times or total time when a threshold value is exceeded, and a time integral of the signal.

This method performs dispensing operation failure judgment by comparing a component of a registered signal waveform with that of a signal waveform to be judged. In this case, one or more components are compared.

Details of the method will be explained below. A method when a time integral of an analog signal will be explained below. The method calculates a time integral value from the signal waveform to be judged and compares the calculated value with a time integral value based on a registered setup value according to a flow chart shown in FIG. 9. The setup value in this case is based on a dispensing quantity registered by the operator. The method determines whether or not the time integral value calculated from the signal waveform to be compared corresponds to a normal or failed dispensing operation to perform dispensing operation failure judgment. In this example, the time integral of the signal is used as a signal waveform component. However, it is also possible to use other components (the measurement time, the maximum output value, the output value at arbitrary time, the total number of times or total time when a threshold value is exceeded). Further, as means for judging a failure, judgment means for failure judgment based on the result of capacitance measurement explained in FIGS. 3A to 3C is used.

As dispensing operation failure judgment means, i.e., means for detecting a suction failure accompanying aeration during the suction operation, a method of using a capacitance between the dispensing probe and a cassette or a cassette holder in a section from the start to the end of the solution dispensing has been explained. This method is applicable to process failure judgment by measuring a capacitance between the dispensing probe and a frame ground in another process other than the dispensing operation.

As disclosed in JP-A-8-114604, a liquid dispensing apparatus which detects a liquid surface based on a capacitance, checks the existence of a solution in a cassette, and performs the suction operation is known. A method of calculating a cross-sectional area of a cassette from a waveform of a liquid surface detection signal and applying it to process the failure detection will be explained below.

Here, this method makes use of the fact that a signal waveform used when the probe of the reagent pipettor 110 detects a liquid surface in a reagent bottle 112 depends on the bottle cross-sectional area. The reagent bottle 112 is arranged on the rotatable reagent compartment 125. A predetermined quantity of reagent is dispensed from the reagent bottle 112 by the probe of the reagent pipettor attached to the movable arm of the reagent pipettor 110 into the vessel 106. With this reagent dispensing operation, the probe of the reagent pipettor sucks a reagent at a reagent suction position. Before reagent suction, the reagent compartment 125 transfers the reagent bottle to the reagent suction position. If reagent suction is performed immediately after the reagent bottle is transferred by the rotation of the reagent compartment, shaking of the solution in the bottle is determined by the rotational speed and moving distance of the reagent compartment, the viscosity of the solution, and other conditions.

Then, a partition plate may be provided in the bottle in order to reduce shaking of the solution when the bottle is transferred. The cross-sectional area required when the probe of the reagent pipettor 110 detects a liquid surface in the reagent bottle 112 when a partition plate is provided in the bottle is smaller than that otherwise. A signal waveform when a liquid surface in the reagent bottle 112 is detected depends on the bottle cross-sectional area.

Therefore, the second embodiment of the present invention performs the steps of: calculating a bottle cross-sectional area to be subjected to comparison based on a relation between the bottle cross-sectional area and a signal change before or after the probe comes in contact with the reagent in the reagent bottle; and performing bottle arrangement failure judgment by comparing the calculated value with a registered bottle cross-sectional area. The cross-sectional area to be compared is based on a bottle setup (size of the bottle, registered place) registered in advance by the operator. The operator arranges a reagent bottle 112 on the registered place, and therefore the bottle cross-sectional area is judged as normal if the bottle is correctly arranged.

Since the quantity of reagent used differs for each reagent subjected to analysis, the quantity of reagent loaded differs for each reagent. Further, analysis items include an analysis item requiring only one kind of reagent and an analysis item requiring a plurality of different reagents. Therefore, in order to simultaneously measure a plurality of analysis items, a plurality of reagent bottles 112 are arranged on the reagent compartment 125; however, it is necessary for an apparatus manufacturer to take measures for effectively arranging reagent bottles 112 based on a difference in the quantity of reagent used and a combination of reagents (one or a plurality of kinds of reagents) for each item. Also in this case, partitioning a bottle with a partition plate is an effective means for arranging a plurality of reagents on an arrangement area of the bottle. However, the bottle may have a predetermined orientation when it is placed and therefore the operator may arrange a bottle in an improper orientation.

With the bottle partitioned by a partition plate into two areas having different cross-sectional areas, when the probe of the reagent pipettor 110 detects a liquid surface in the reagent bottle 112, if the capacitance sensor 201 implemented in the probe measures a capacitance between the probe and the reagent bottle 112 or the reagent compartment 125, a capacitance according to the bottle cross-sectional area is obtained. The present embodiment performs the steps of: calculating a bottle cross-sectional area to be judged based on a relation between the bottle cross-sectional area and a capacitance before or after the probe comes in contact with the reagent in the reagent bottle; and performing failure judgment of arrangement place and orientation of a reagent bottle by comparing the calculated cross-sectional area with a bottle setup registered by the operator. As a result of the failure judgment, if the arrangement place or the orientation is wrong, the operator is informed of the failure with an alarm.

If a signal waveform based on the cross-sectional area is registered, it can be used for bottle cross-sectional area failure judgment from the result of capacitance measurement. Judgment means for failure judgment based on the result of capacitance measurement explained in FIGS. 3A to 3C is used as means for judging a failure. Although the present embodiment calculates a cross-sectional area of a cassette from a waveform of a liquid surface detection signal for reagent bottle, it is applicable to a sample cassette, a vessel, and other cassettes for storing a solution.

As another embodiment for detecting a process failure by measuring a capacitance between the probe and the frame ground in a process, the present embodiment performs reagent failure judgment based on a capacitance of surface detection for the reagent. This method makes use of the fact that a signal waveform when the probe of the reagent pipettor 110 detects a liquid surface in the reagent bottle 112 is reagent dependent.

A third embodiment of the present invention measures a capacitance when the dispensing probe detects a liquid surface in a cassette and determines a reagent by use of a measurement result. A method of discriminating a reagent performs the steps of: registering a capacitance before or after the probe comes in contact with a reagent is registered in relation to a reagent used by the apparatus; comparing the registered value with a signal waveform to be judged; and performing reagent failure judgment by comparing the result of reagent discrimination with a setup value registered by the operator. Judgment means for failure judgment based on the result of capacitance measurement explained in FIGS. 3A to 3C is used as means for judging a failure.

In accordance with the present invention, if the operator erroneously arranges an analysis item $R_2$ as an analysis item $R_1$ registered in the apparatus, a reagent bottle arrangement error can be detected through reagent failure judgment. Although the present embodiment performs reagent failure judgment from a waveform of a liquid surface detection signal for reagent bottle, it is applicable also to a sample cassette subjected to measurement. Although an embodiment for a reagent has been explained above, the present embodiment is effective also for a sample.

Further, another embodiment for process failure detection by measuring a capacitance between the probe and the frame ground in a process performs washing failure judgment from a signal waveform during a probe washing operation. A signal waveform when the probe of the reagent pipettor 110 is washed with cleaning water depends on the cleaning water conditions (washing time, washing direction, washing range, amount of water, and cleaning water type).

In accordance with a fourth embodiment of the present invention, when a capacitance between the dispensing probe currently being washed and a washing tub (not shown) is measured, a signal change based on the cleaning water conditions is obtained before or after the probe comes in contact with the cleaning water. As a method of washing the probe with cleaning water, when cleaning water is supplied by a pump (not shown), the quantity of cleaning water is controlled by a supply pressure of the pump (not shown) and opening and closing of the valve. However, if an air bubble exists in the passage and pressure fluctuations by the air bubble are not greater than a measurement limit of a pressure gauge (not shown), the quantity of cleaning water cannot be controlled possibly resulting in insufficient washing.

As measures against this, the present embodiment performs the steps of: registering a relation between the quantity of cleaning water and a capacitance in the apparatus; calculating a quantity of water based on the result of measurement of the capacitance between the probe and the washing tub (not shown); and controlling the quantity of cleaning water based on the result of calculation. The present embodiment applies the solution quantity failure judgment to the cleaning water quantity control.

As a method of washing the probe with cleaning water, when the probe is immersed in the washing tub (not shown) and the outer wall of the probe is washed with a flow of the cleaning water, washing depends on the washing time, in other words, the time of immersion of the probe into the washing tub (not shown) and the washing range of the probe. In this case, this method performs the steps of: registering a relation between the washing time or the washing range and a capacitance in the apparatus; calculating a washing time or a washing range based on the result of measurement of the capacitance between the probe and the washing tub (not shown); and performing washing failure judgment based on this information. In accordance with each of the above-mentioned embodiments regarding probe washing, similarly to the second embodiment, judgment means for failure judgment based on the result of capacitance measurement explained in FIGS. 3A to 3C is used for washing failure judgment.

A relation between a result of dispensing operation failure judgment through capacitance measurement and the absorbance of mixture of a sample and a reagent will be explained below based on a measurement result. Results of the dispensing operation failure judgment are shown in FIG. 4.

The above-mentioned measurement was performed under a condition that the liquid surface immersion depth of the reagent probe becomes shallow so that aeration, etc. during the suction operation easily occurs when the dispensing probe sucks a solution, and that the operating range and the speed of the reagent compartment having a reagent cassette thereon are maximized so that the liquid surface waves during the reagent suction operation. While the reagent probe is dispensing a reagent into a cassette, a capacitance between the nozzle and a cassette holder for holding a cassette for storing a solution was measured and the dispensing operation failure judgment was performed. Judgment means for failure judgment based on the result of capacitance measurement explained in FIGS. 3A to 3C is used as a method of discriminating a failure.

FIG. 4 shows the number of tests, the absorbance, a result of waveform failure judgment in an analog signal, a result of waveform failure judgment in a digital signal, and a result of the dispensing operation failure judgment. When a waveform failure is judged, o is marked; otherwise, x is marked. Further, in the dispensing operation failure judgment, if the analog signal or the digital signal contains a waveform failure, the result is failure; otherwise, the result is normal.

The absorbance when the dispensing operation is judged as Failure was higher than that when the dispensing operation is judged as Normal. For example, the absorbance in the case of normal suction operation is 8670 mAbs. (test 1) and 9337 mAbs. (test 2) in the case of failed suction operation.

The result shown in FIG. 4 was obtained in a state where reagent cassettes were diagonally arranged on the reagent compartment to allow shaking of the reagent solution in each of the reagent cassettes with the rotation of the reagent compartment and then the reagent probe dispensed the solution alternately from each of the reagent cassettes. Aeration during the suction operation, etc. occurs also in a state where the liquid surface has bubbled.

Figure 10:
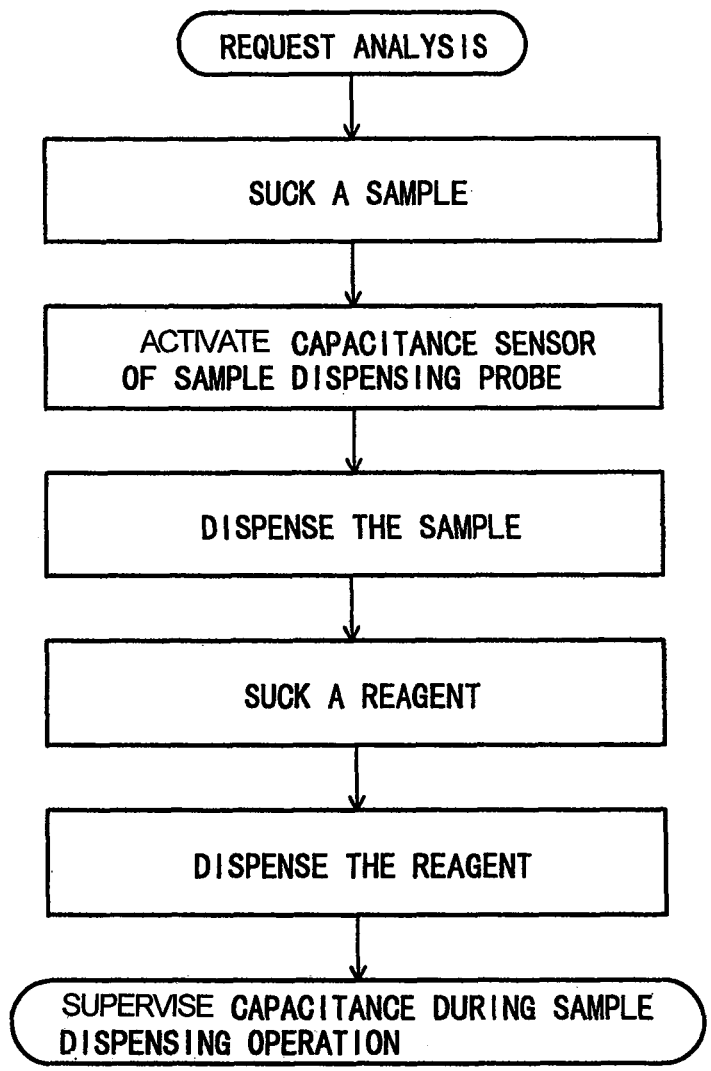
FIG. 10 is a diagram showing a flow chart up to capacitance measurement during sample dispensing operation according to the first embodiment of the present invention.

The result of FIG. 4 was obtained by measuring a capacitance while the reagent probe is dispensing a reagent into a cassette and performing the reagent dispensing operation failure judgment based on the measurement result. As shown in flow charts of FIGS. 10 and 11, it may be possible to apply the measurement result to the sample dispensing operation failure judgment.

Figure 11:
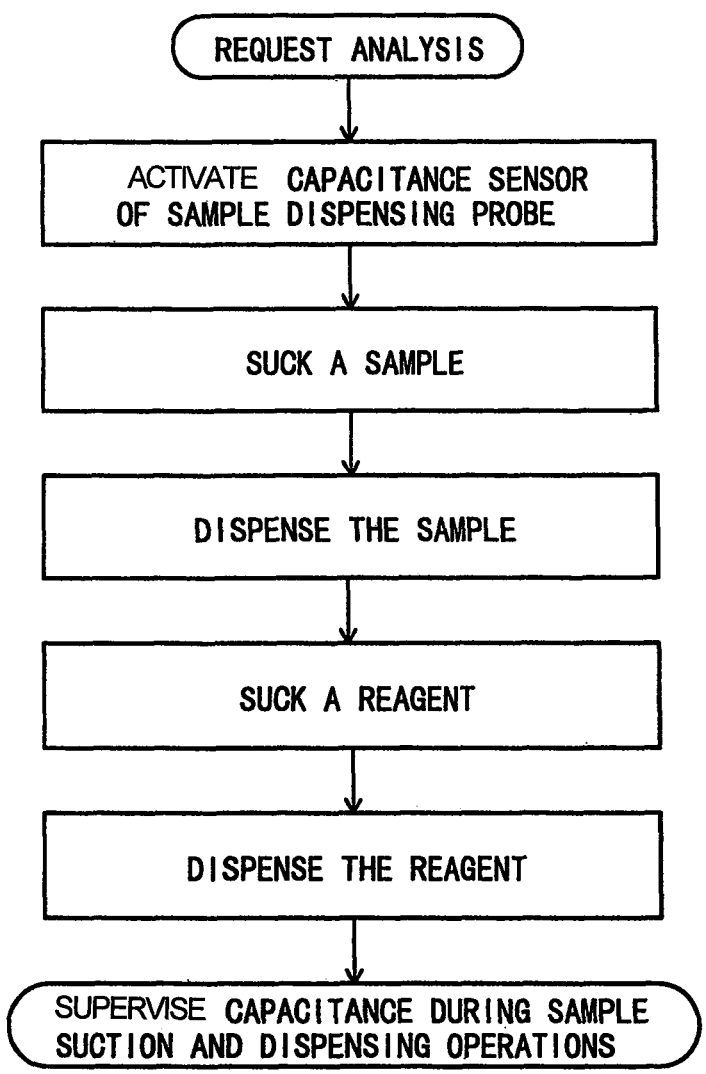
FIG. 11 is a diagram showing a flow chart for measuring a capacitance during sample suction and dispensing operations according to the first embodiment of the present invention.
Figure 12:
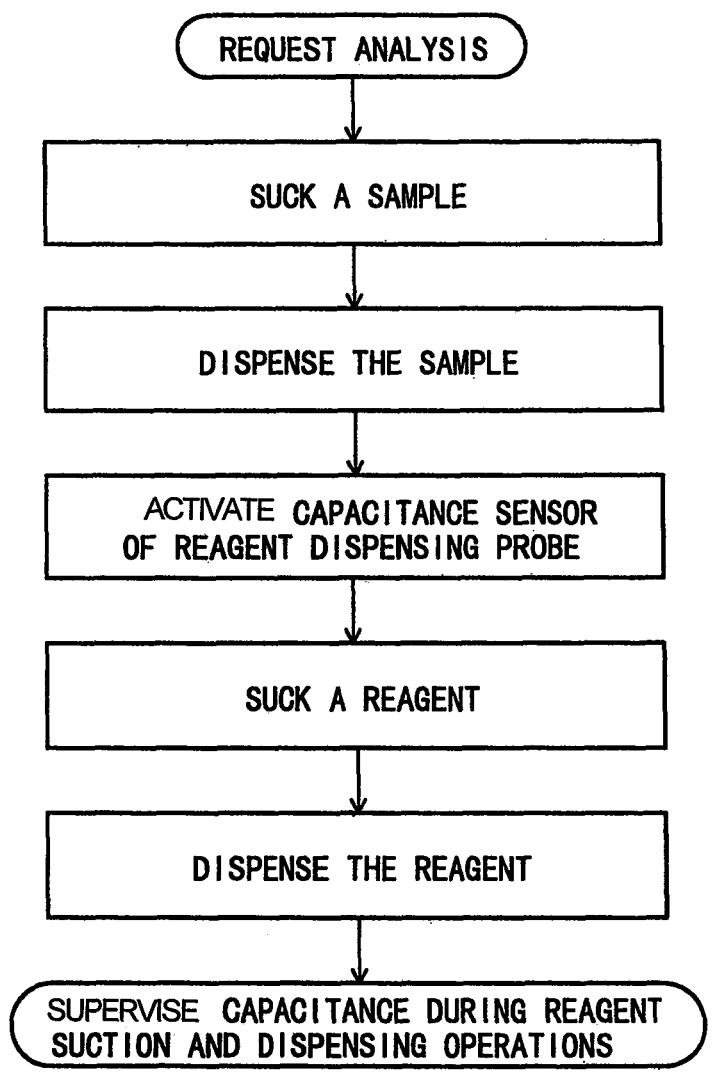
FIG. 12 is a diagram showing a flow chart for measuring a capacitance during reagent suction and dispensing operations according to the first embodiment of the present invention.

Further, as shown in flow charts of FIGS. 11 and 12, it may be possible to measure a capacitance during the suction and solution dispensing operations.

Either method makes it possible to attain dispensing operation failure judgment with higher accuracy in comparison with the methods that have been proposed.

As mentioned above, the present invention is advantageous in that it is capable of correctly detecting a dispensing operation failure with high accuracy by use of means for measuring an electrical physical quantity between the nozzle side and the cassette or cassette holder side.

Further, the present invention is advantageous in that it is capable of detecting a failure simply by using the nozzle side and the cassette or cassette holder side as electrodes without particularly using a complicated detection mechanism or means.

An application to be activated when the result of the dispensing operation failure judgment is failure will be explained below.

This application automatically adds an alarm to an analysis result in which a result other than an expected value may be output when the result of the dispensing operation failure judgment is failure, and outputs the analysis result having information about the possibility of deviation from the expected value.

Figure 7:
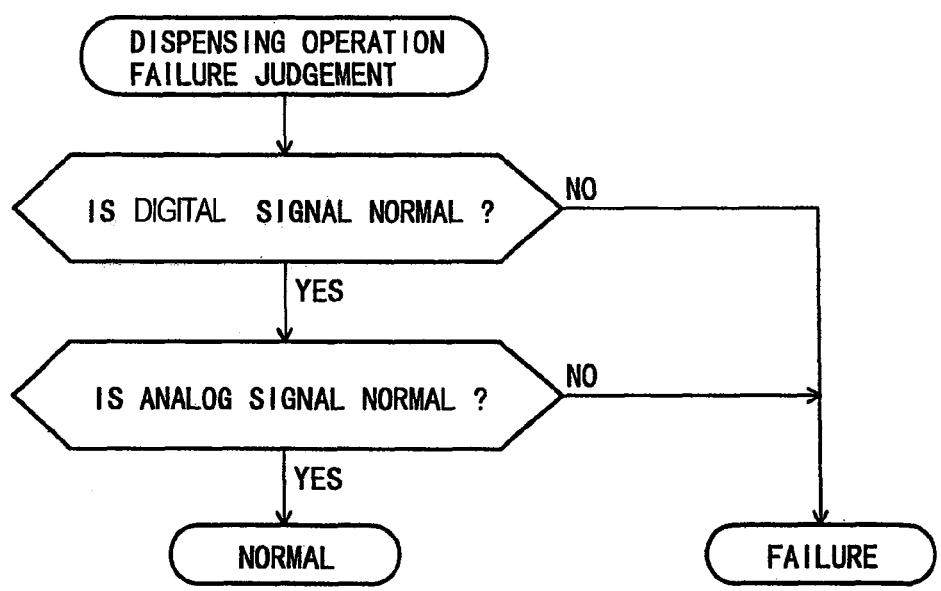
FIG. 7 is a diagram showing a flow chart for performing dispensing operation failure judgment according to the first embodiment of the present invention.
Figure 8:
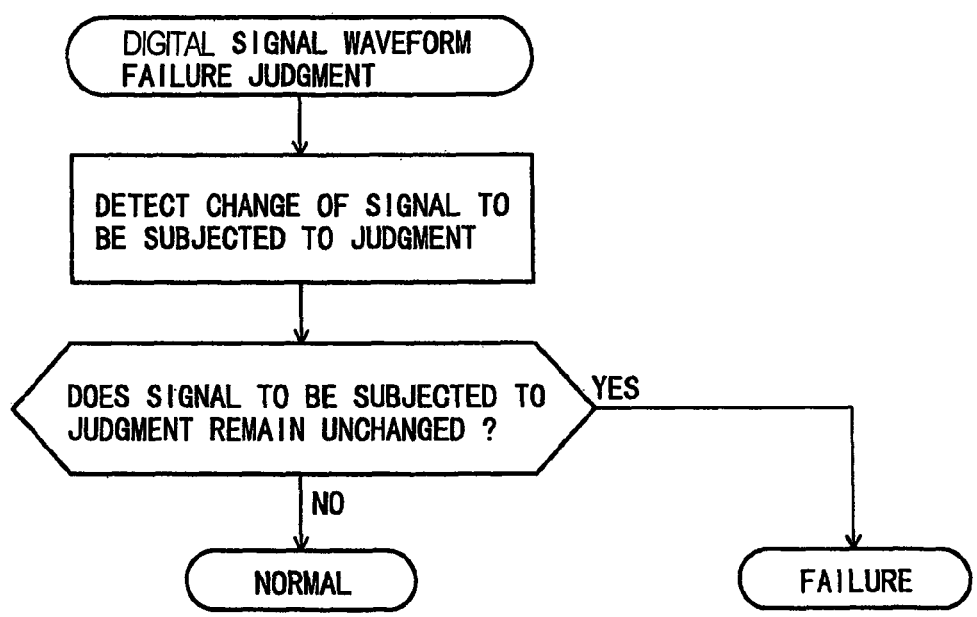
FIG. 8 is a flow chart showing an example of means for digital signal failure judgment out of dispensing operation failure judgment according to the first embodiment of the present invention.
Figure 9:
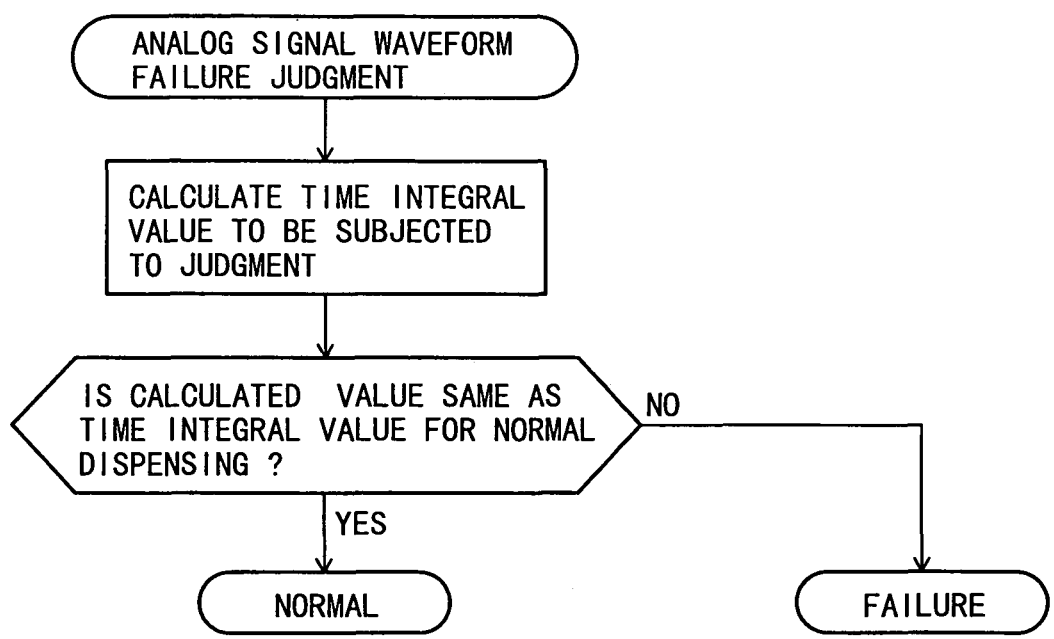
FIG. 9 is a flow chart showing an example of means for analog signal failure judgment out of dispensing operation failure judgment according to the first embodiment of the present invention.

For example, the application performs failure detection in the dispensing operation according to flow charts shown in FIGS. 7, 8, and 9.

As an example of application to be activated when the result of above-mentioned dispensing operation failure judgment is Failure, it is possible to easily configure a system which adds an alarm to an analysis result in which a result other than the expected value may be output, when the result of the dispensing operation failure judgment is Failure, and further masks the analysis result (not to allow the result to be output) to prevent a result other than the expected value from being reported.

In accordance with embodiments of the present invention, a dispensing operation failure can be detected when the dispensing probe dispenses a sample or a reagent, and therefore it is possible to inform the operator of a result other than the expected value before a measurement result is obtained.

Therefore, the operator can make a request on a reinspection of a target item earlier than previously known.

Further, this application is used when the result of the dispensing operation failure judgment is failure. It makes it possible to automate operations up to the time when the operator performs reinspection.

As an example of this case, the application displays a dispensing failure alarm on an alarm display screen. Further, it may be possible to append information about the possibility of a difference from the expected value to an analysis result; display an analysis failure alarm in the analysis result display screen; automatically request reinspection of a relevant inspection; and display a message dialog for notifying the operator of an acknowledgement for the reinspection request.

An application to be activated when failure judgment on reagent bottle cross-sectional area is performed in residual reagent quantity registration will be explained below. Failure judgment on reagent bottle cross-sectional area is a second embodiment of the present invention, wherein a capacitance between the probe and a reagent bottle is measured in residual reagent quantity registration, and a measurement result is used for judgment.

Figure 13:
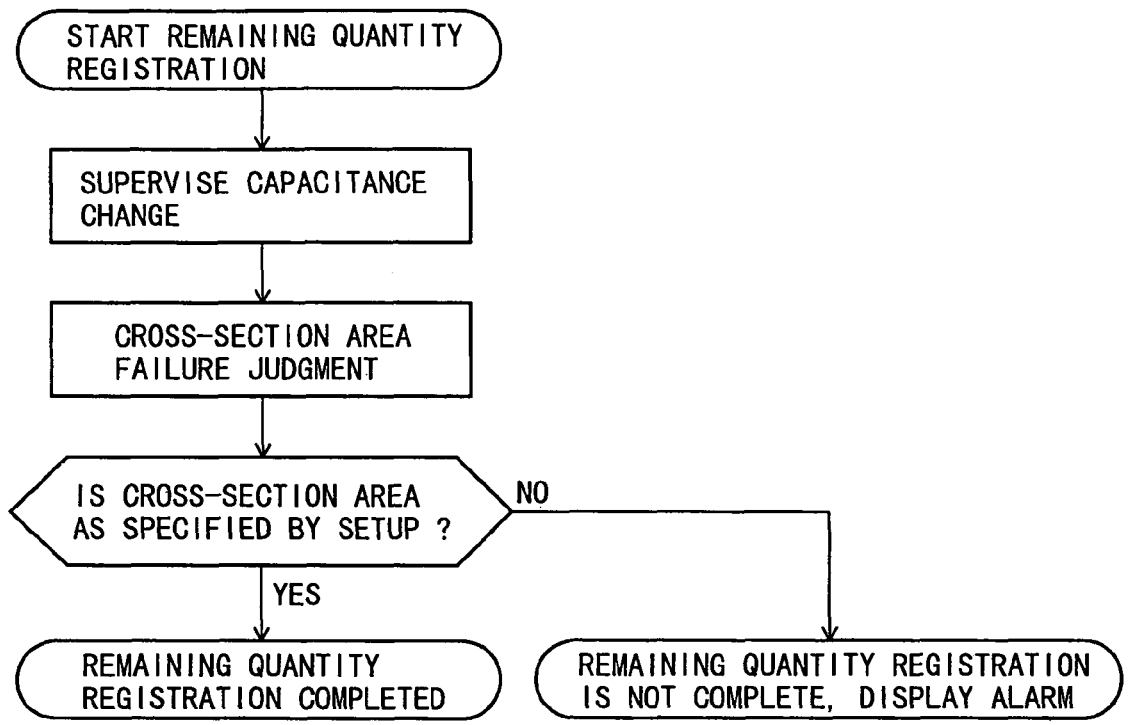
FIG. 13 is a diagram showing a flow chart from the start of residual reagent quantity registration up to result display according to a second embodiment of the present invention.
Figure 14:
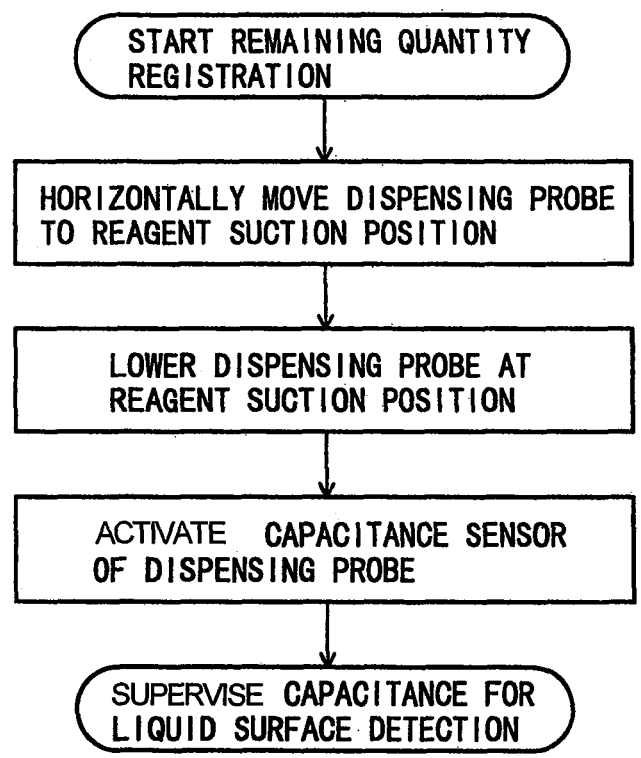
FIG. 14 is a diagram showing a flow chart of apparatus operation from the start of residual quantity registration in residual reagent quantity registration according to the second embodiment of the present invention.
Figure 15:
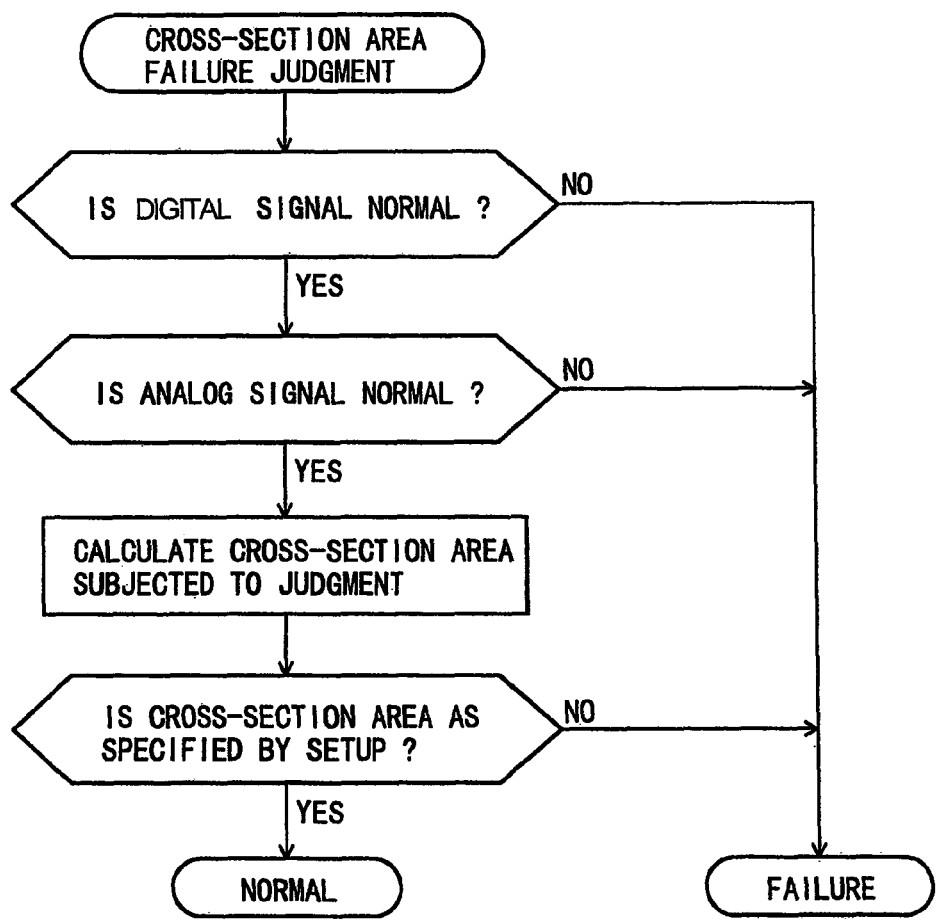
FIG. 15 is a diagram showing a flow chart for performing failure judgment on reagent bottle cross-sectional area in residual reagent quantity registration according to the second embodiment of the present invention.

When the result of failure judgment on reagent bottle cross-sectional area is failure, the application recognizes the relevant residual quantity registration as not complete and does not display the relevant residual quantity on the reagent registration screen. For example, if the information registered by the operator before residual quantity registration is residual quantity 0, the relevant reagent residual quantity is left unchanged (residual quantity 0). At the same time, a reagent bottle cross-sectional area failure is notified to the alarm display screen. On the other hand, when the result of failure judgment on reagent bottle cross-sectional area is Normal, the result of the relevant residual quantity registration is displayed. The above-mentioned failure judgment on reagent bottle cross-sectional area is performed according to flow charts shown in FIGS. 13 and 15.

An application to be activated when reagent failure judgment is performed in residual reagent quantity registration will be explained below. Reagent failure judgment is a third embodiment of the present invention, wherein a capacitance between the probe and a reagent bottle is measured in residual reagent quantity registration, and a measurement result is used for judgment.

Figure 16:
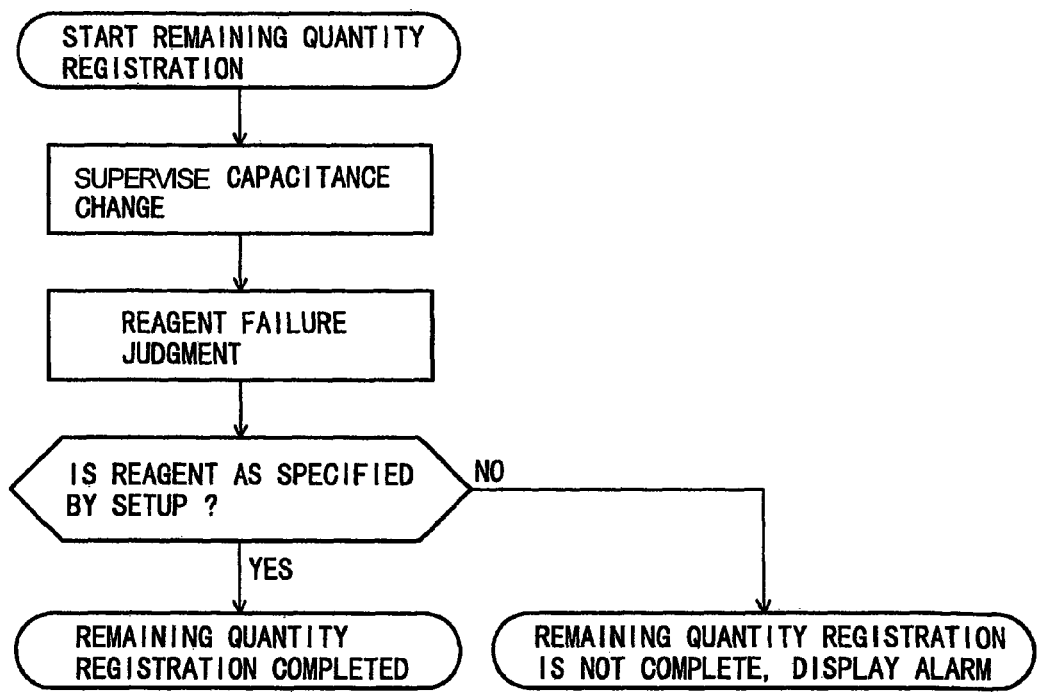
FIG. 16 is a diagram showing a flow chart from the start of residual reagent quantity registration up to result display according to a third embodiment of the present invention.
Figure 17:
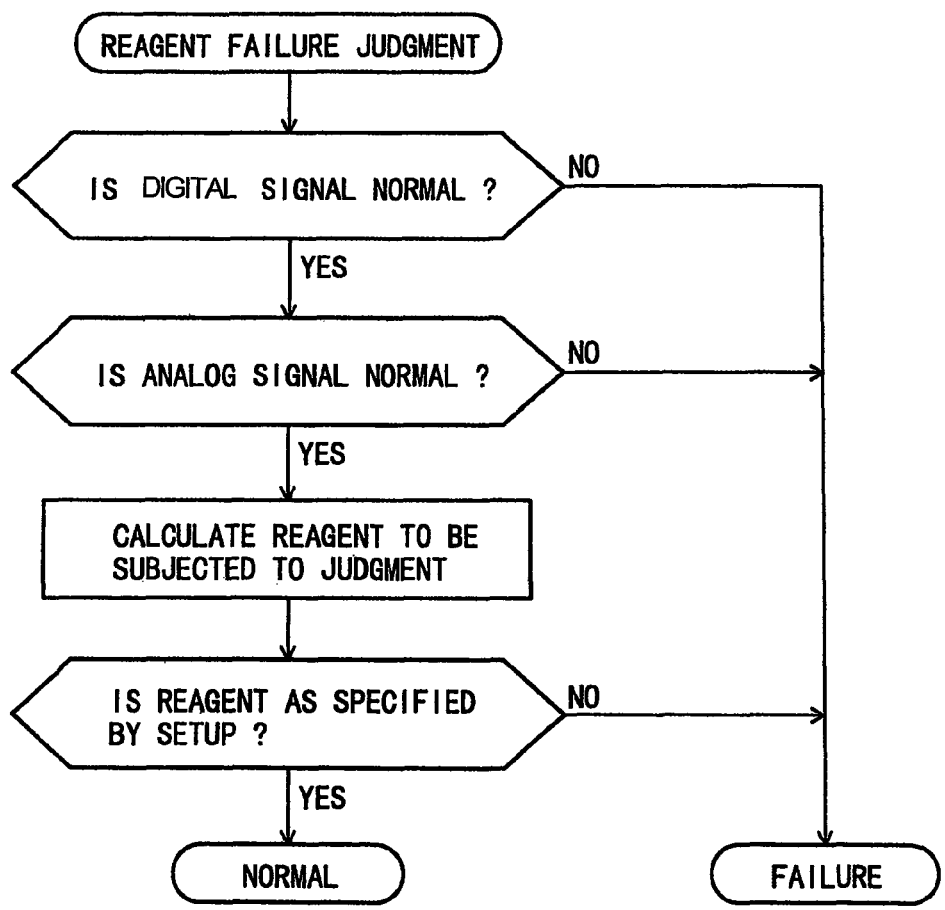
FIG. 17 is a diagram showing a flow chart for performing reagent failure judgment in residual reagent quantity registration according to the third embodiment of the present invention.

When the result of reagent failure judgment is failure, the application recognizes the relevant residual quantity registration as not complete and does not display the relevant residual quantity on the reagent registration screen. For example, if the information registered by the operator before residual quantity registration is residual quantity 0, the relevant reagent residual quantity is left unchanged (residual quantity 0). At the same time, a relevant reagent failure is notified to the alarm display screen. On the other hand, when the result of reagent failure judgment is normal, the result of residual quantity registration of the relevant reagent is displayed. The above-mentioned reagent failure judgment is performed according to flow charts shown in FIGS. 16 and 17.

An application to be activated when washing failure judgment is performed in dispensing probe washing will be explained below. Washing failure judgment is a fourth embodiment of the present invention, wherein a capacitance between the probe and a washing tub is measured, and a measurement result is used for judgment.

Figure 18:
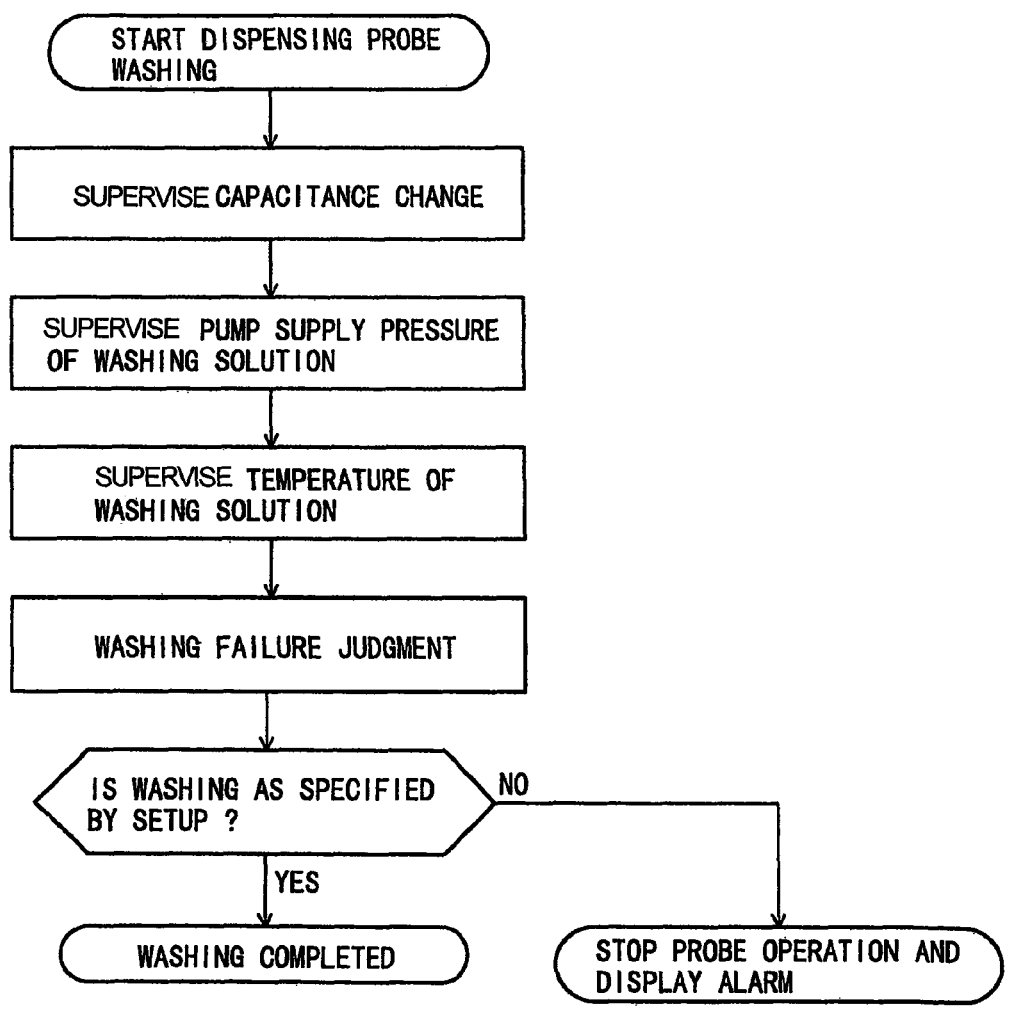
FIG. 18 is a diagram showing a flow chart from the start to the end of dispensing probe washing according to a fourth embodiment of the present invention.
Figure 19:
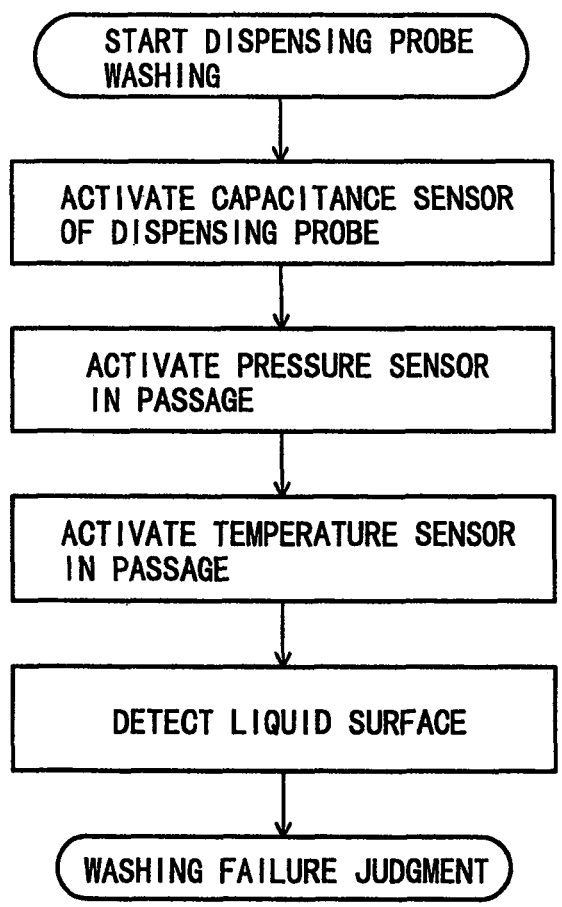
FIG. 19 is a diagram showing a flow chart from the start of dispensing probe washing up to washing failure judgment according to the fourth embodiment of the present invention.
Figure 20:
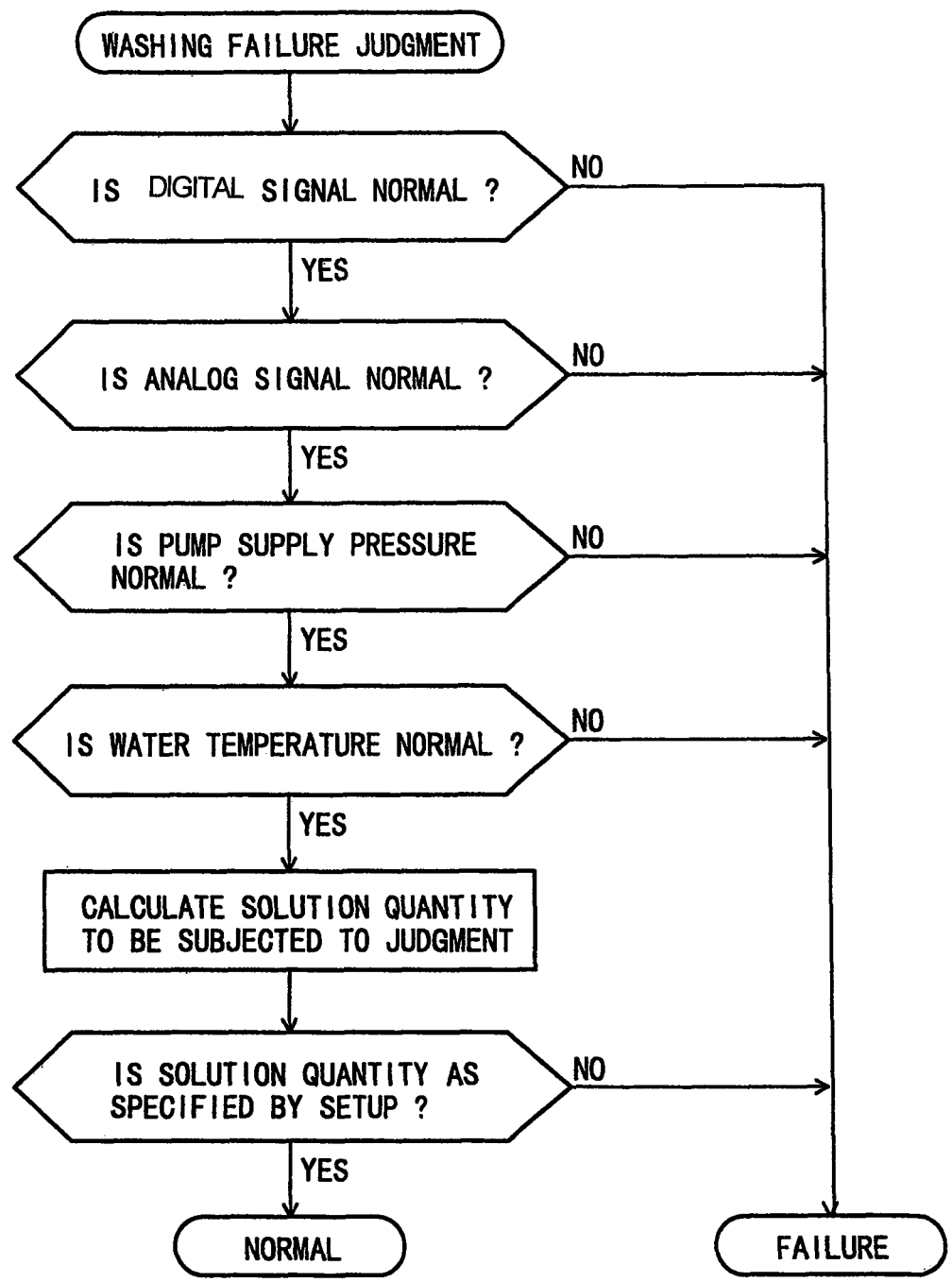
FIG. 20 is a diagram showing a flow chart for performing washing failure judgment in dispensing probe washing according to the fourth embodiment of the present invention.

When the result of dispensing probe washing failure judgment is failure, the application recognizes the relevant washing operation as not complete and stops a series of probe operations from dispensing to washing. This prevents contamination from previous relevant washing to the next dispensing operation, accompanying dispensing probe washing failure judgment. In this case, a dispensing probe washing failure is displayed on the alarm display screen at the same time. On the other hand, when the result of judgment is normal, the dispensing probe proceeds to the following operation. The above-mentioned dispensing probe failure judgment is performed according to flow charts shown in FIGS. 18, 19, and 20.

What is claimed is:

1. A liquid dispensing apparatus of an automatic analyzer comprising:
    a nozzle which sucks a solution in a cassette and discharges the sucked solution into another cassette, where the nozzle is a first electrode;
    a cassette holder which holds the another cassette, where the cassette holder is a second electrode;
    a measurement sensor to measure capacitance between the first electrode and second electrode during a dispensing operation of the nozzle;
    a computer which judges whether or not there is a failure of the dispensing operation from a change in the capacitance; and
    a display unit which displays a result of judgment as to the failure of the dispensing operation from the computer,
    wherein the computer judges whether or not the failure of the dispensing operation has occurred with an analog signal of the change in the capacitance when no failure of the dispensing operation is judged using a digital signal of the change in the capacitance, and
    the computer does not judge whether or not the failure of the dispensing operation has occurred with the analog signal of the change in the capacitance when the failure of the dispensing operation is judged using the digital signal of the change in the capacitance.

2. A liquid dispensing apparatus of an automatic analyzer comprising:
    a nozzle which sucks a solution in a cassette and discharges the sucked solution into another cassette, where the nozzle is a first electrode;
    a cassette holder which holds the another cassette, where the nozzle is used as a first electrode and a second electrode is disposed on a cassette holder side of the liquid dispensing apparatus, where the cassette holder side includes a second electrode;

a measurement sensor to measure capacitance between the first electrode and second electrode during a dispensing operation of the nozzle;

a computer which judges whether or not there is a failure of the dispensing operation from a change in the capacitance; and a display unit which displays a result of judgment as to the failure of the dispensing operation from the computer, wherein the computer judges whether or not the failure of the dispensing operation has occurred with an analog signal of the change in the capacitance when no failure of the dispensing operation is judged using a digital signal of the change in the capacitance, and the computer does not judge whether or not the failure of the dispensing operation has occurred with the analog signal of the change in the capacitance when the failure of the dispensing operation is judged using the digital signal of the change in the capacitance.

3. The liquid dispensing apparatus according to claim 2, wherein:

the measurement sensor also measures capacitance when the nozzle sucks a solution in the cassette.

4. The liquid dispensing apparatus according to claim 2, wherein the second electrode is disposed on the cassette holder.

5. The liquid dispensing apparatus according to claim 2, wherein the second electrode is disposed on the another cassette.

* * * * *